US00PP19162P3

(12) United States Plant Patent
McCully

(10) Patent No.: US PP19,162 P3
(45) Date of Patent: Aug. 26, 2008

(54) ***×WILSONARA RED PACIFIC* PLANT NAMED 'DEEP SHADOWS'**

(50) Latin Name: *×Wilsonara Red Pacific*
Varietal Denomination: Deep Shadows

(76) Inventor: James McCully, 2146 Kaumana Dr., Hilo, HI (US) 96720

( * ) Notice: Subject to any disclaimer, the term of this patent is extended or adjusted under 35 U.S.C. 154(b) by 0 days.

(21) Appl. No.: 11/651,328

(22) Filed: Jan. 5, 2007

(65) Prior Publication Data

US 2008/0184434 P1 Jul. 31, 2008

(51) Int. Cl.
*A01H 5/00* (2006.01)

(52) U.S. Cl. ..... Plt./311

(58) Field of Classification Search ..... Plt./311
See application file for complete search history.

*Primary Examiner*—Kent L. Bell
*Assistant Examiner*—June Hwu

(57) ABSTRACT

A new variety of orchid plant of the Oncidiinae Intergenerics, ×*Wilsonara,* named ×*Wilsonara* Red Pacific 'Deep Shadows', distinguished particularly by a compact size, many deep red flowers round in shape arranged pleasingly on a panicle and growing quickly to sexual maturity.

2 Drawing Sheets

Latin name of the genus and grex of the plant claimed: The Latin name of the genus and grex of the plant claimed is ×*Wilsonara* Red Pacific.

Variety denomination: The present invention comprises a new and distinct cultivar of ×*Wilsonara* orchid, and hereinafter referred to by the cultivar name ×*Wilsonara* Red Pacific 'Deep Shadows'.

BACKGROUND OF THE INVENTION

×*Wilsonara* is an artificial hybrid of orchids between three genera in the subtribe Oncidiinae. ×*Wilsonara* is made from the genera *Odontoglossum,* consisting of about 300 species, *Oncidium,* consisting of about 500 species and *Cochlioda,* consisting of 6 species. The first hybrid of ×*Wilsonara* was created in 1916. Due to the varying percentages of the parent genera that make up ×*Wilsonara* and the gene expression in their progeny, ×*Wilsonara* varies in morphology and size. All exhibit sympodial growth habit.

×*Wilsonara* breeding is typically done from sexual methods. Asexual propagation of ×*Wilsonara* is often done in aseptic tissue culture from apical or axillary shoots.

The new cultivar was discovered by the Inventor within the progeny of a cross made by the Inventor on Sep. 8, 1999. The Inventor selected ×*Wilsonara* Red Pacific 'Deep Shadows' as a single plant from a population of over 50 plants grown in Hilo, Hi. ×*Wilsonara* Red Pacific 'Deep Shadows' was submitted by the Inventor to a commercial tissue culture laboratory in Bangkok, Thailand on Jun. 10, 2003 and asexually reproduced by aseptic tissue culture technique. A quantity was produced for evaluation and has demonstrated that the unique combination of characteristics as herein disclosed for the new cultivar are firmly fixed and are retained through successive generations of asexual reproduction.

Other seedlings from the same cross that was used to produce ×*Wilsonara* Red Pacific 'Deep Shadows' have been commercially available from others. The characteristics of ×*Wilsonara* Red Pacific 'Deep Shadows' are clearly distinguishable from the characteristics of those other plants. Those other plants were sold without specific epithet to individuals and other nurseries. To the Inventor's knowledge, the only other named clone of the cross is ×*Wilsonara* Red Pacific 'Ruby Red', non-patented, and is owned by the Inventor. Plants of the grex ×*Wilsonara* Red Pacific are sold as plants of the grex without specific epithet.

BRIEF SUMMARY OF THE INVENTION

The following traits have been repeatedly observed and are determined to be basic characteristics of the new cultivar which in combination distinguish this ×*Wilsonara* orchid as a new and distinct cultivar:

Flowers of the new cultivar are deep blood red on the column, sepals and petals. The labellum is bright red. The anther cap is white with a red spot near the bottom 1 millimeter (mm) wide and 2 mm long. As the flower ages, the anther cap develops bright pink spots that are less than 1 mm. The natural horizontal spread is 4.7 centimeters (cm); natural vertical spread is 4.8 cm; sepal width 1.6 cm; sepal length 1.6 cm; petal width 1.5 cm; petal length 2.3 cm; labellum width 2.0 cm; labellum length 2.3 cm. There are around 25 to 35 flowers on the first bloom depending on the plant's environment.

Inflorescence is a basal panicle, approximately 51 cm tall with 5 to 7 alternate lateral. The branching of the panicle starts right above the leaves and the branches vary in length from 14 cm at the bottom branch to 3 to 7 cm at the top branch. The size of the inflorescence is appropriate to the overall size of the plant and typical pot size for this cultivar.

There are generally four leaves on the mature pseudobulb, two from the apex and two from the base of the pseudobulb. The apical leaves measure 28 to 37 cm and are 2.5 to 4 cm wide. The leaves from the base of the pseudobulb measure up to 36 cm and are 3.5 cm wide. Axillary leaves, or bracts, are sometimes present below the leaves at the base of the pseudobulb. When present, there are usually two each on either side of the pseudobulb and measure 10 to 15 cm long, appearing as a bract. The shape of the leaf is subulate and lanceolate and they are semi-conduplicate at the base. The texture and substance is smooth, waxy and thin. The plants of ×*Wilsonara* Red Pacific 'Deep Shadows' grow to maturity and flower in approximately 18 months.

Plants of the new cultivar have not been observed under all possible environmental conditions. The phenotype may vary significantly with variations in the environment such as temperature, light intensity, and day length, without however any change in genotype.

Plants of the new cultivar differ primarily from the plants of the parent cultivars in flower color, panicle size, rate of growth and speed to maturation. Perhaps the closest commercial comparison to the new cultivar can be made to seedling-derived *Wilsonara* orchids which are genetically heterogeneous, and typically lack uniformity in growth, vigor, plant habit, and flower quality. Since this reference point has inconsistent characteristics, a direct comparison for ×*Wilsonara* Red Pacific 'Deep Shadows' is not available. The new cultivar is a single genotype asexually propagated via tissue culture; thus, its combined horticultural characteristics listed above are uniform and predictable.

BRIEF DESCRIPTION OF THE DRAWINGS

The drawings show the colors of the new variety as nearly true as possible with an illustration of this type. In the drawings.

DETAILED BOTANICAL DESCRIPTION

Figure 1:
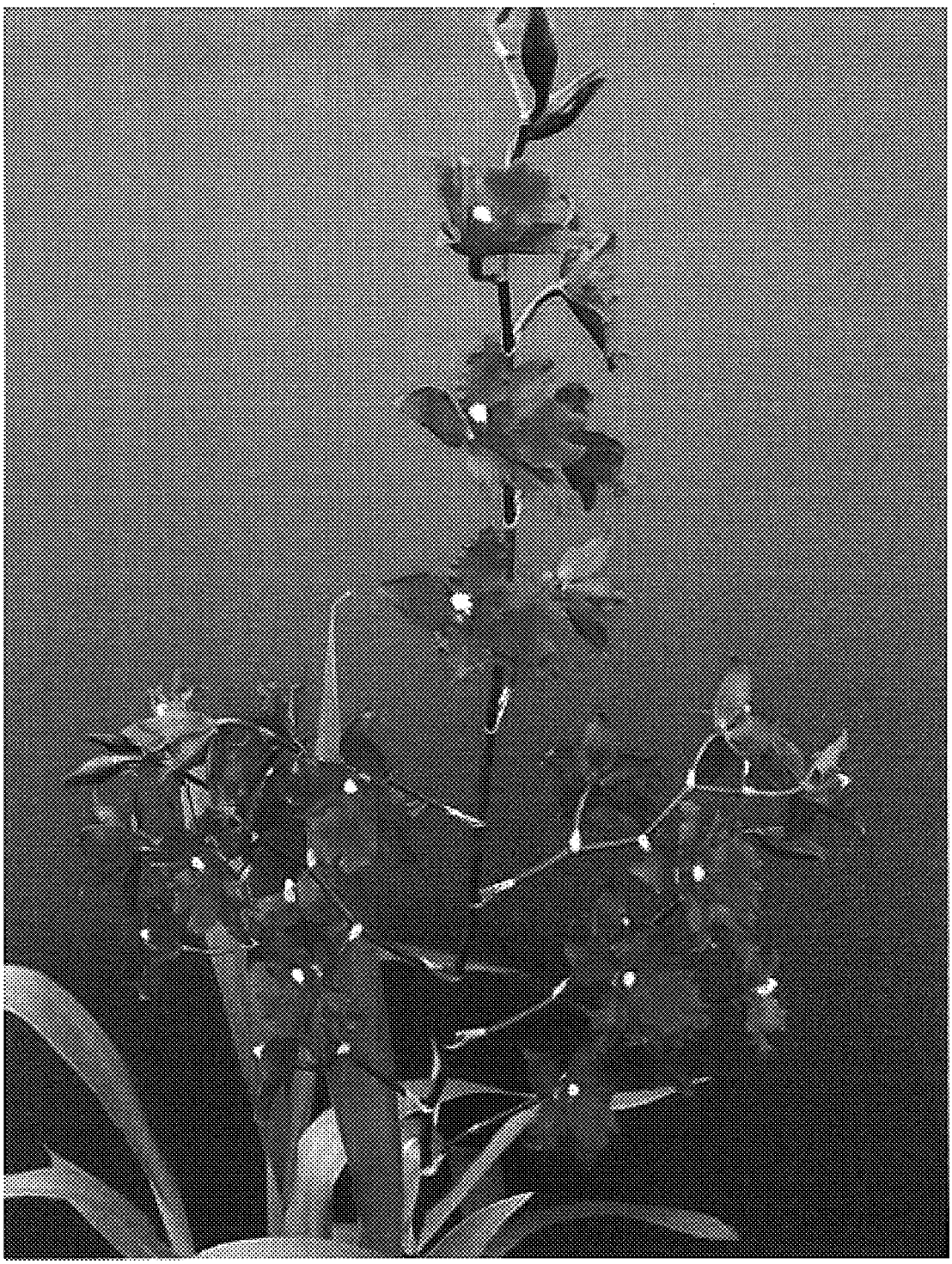
FIG. 1 is a view of the entire plant to reveal the growth habit and general characteristics with its flowers, which is typical of this new variety.
Figure 2:
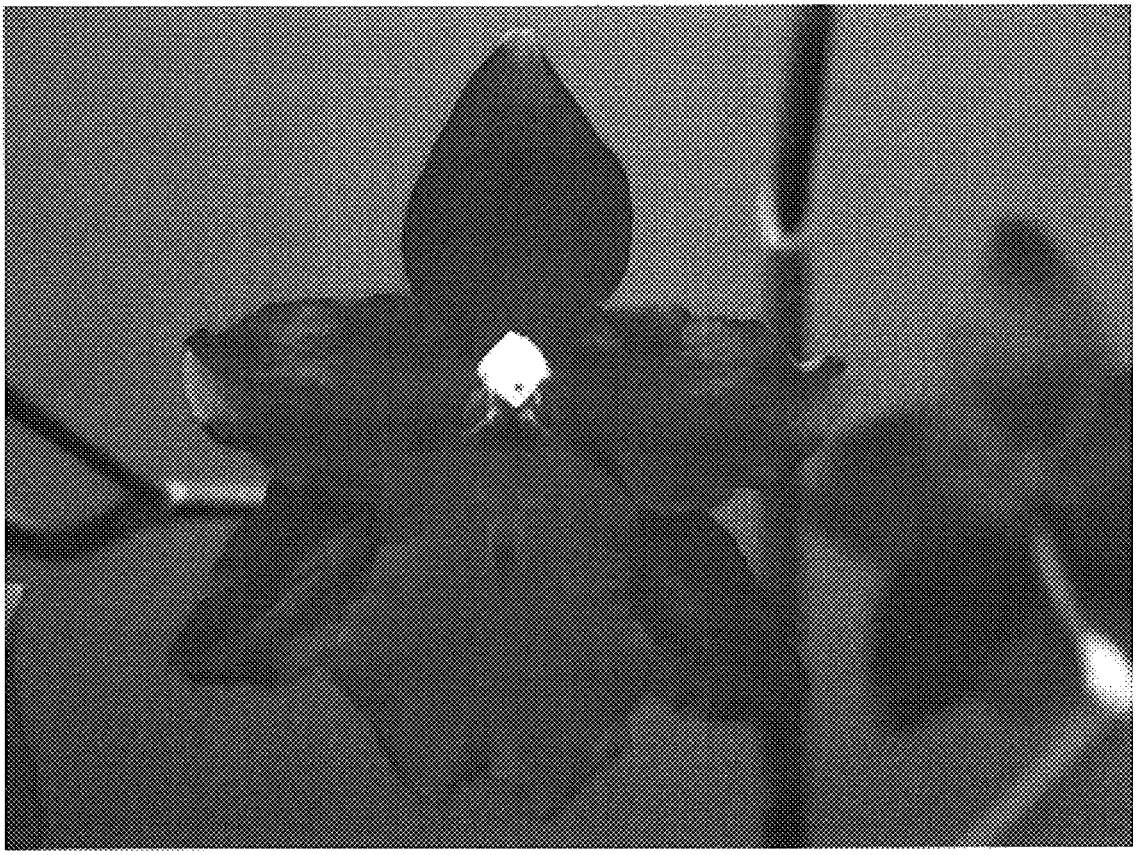
FIG. 2 is a close up view of the flower to show its shape.

All color references are measured against the PANTONE Color System. Colors and numerical measurements are approximate as plant growth and development depends on environmental conditions and cultural practices such as light level, temperature, water quality, fertilization formula and rate, among others, without, however, any variance in genotype.

Plants used for this description are 1 to 2 years in vivo and grown in 2 inch, round green plastic pots, grown in a polycarbonate covered greenhouse in Hilo, Hi., where day temperatures range from 72 to 88 degrees Fahrenheit and night temperatures range from 56 to 72 degrees Fahrenheit. Light levels are between 1500 to 2500 foot candles. This information reflects the annual variations for the area.

Botanical classification: ×*Wilsonara* Red Pacific 'Deep Shadows'.

Parentage: Seedling selected from the cross of the following:

*Seed parent.*—×*Odontocidium* Wildcat 'Bobcat'.

*Pollen parent.*—×*Wilsonara* Lisa Devos 'Carnival'.

Propagation:

*Type.*—Asexual propagation by aseptic tissue culture through axillary shoot initiation.

*Time to initiate and elongate roots in-vivo.*—About 45 days.

*Time to produce fully rooted young plant.*—About 285 days.

Root description: Velamen covered roots, approximately 1.5 mm in diameter, white in color with yellow to green growing tip. The exact shades of white and yellow/green vary greatly with minimal changes in environmental conditions.

Plant description: Under appropriate growing conditions, plants of the new cultivar attain a mature size of about 36 cm in height (top of leaf plane) and about 4 cm in width.

Foliage description:

*Arrangement.*—Sympodial growth habit.

*Quantity of leaves per growth.*—Each sympodial growth has shown four leaves, two on the apex of the pseudobulb and two from the axis at the base of the pseudobulb.

*Leaf length.*—Leaves measure from 28 to 37 cm in length. The axillary leaves at the base of the pseudobulb may be as short as 10 cm and as long as 15 cm.

*Leaf width.*—The width of the leaf is 2.5 to 4 cm.

*Leaf shape.*—The shape is subulate and lanceolate, texture and substance is smooth, waxy and thin.

*Pseudobulb shape.*—The pseudobulb shape is a laterally compressed ovoid.

*Pseudobulb length.*—The pseudobulb is approximately 7 to 8 cm long.

*Pseudobulb width.*—The pseudobulb is approximately 4.5 cm wide and 2.5 cm thick.

*Foliage color.*—Under the described growing conditions, the foliage color on both sides of the leaves is similar to PANTONE 377U (green) of the PANTONE Color System. There is no vein color distinction. The pseudobulb can vary from PANTONE 377U (green) to tinted PANTONE 437C (purple) or PANTONE 377U (green) spotted with PANTONE 262C (purple).

Flower/inflorescence description:

*Description.*—Panicle, approximately 50 cm on a first bloom plant and has 5 to 7 alternate side branches ranging in size from 3 to 14 cm. The branches start just above the leaves and become shorter near the panicle apex. The size of the inflorescence is appropriate to the overall size of the plant and typical pot size for this cultivar.

*Dimensions.*—Flower dimensions are: natural horizontal spread is 4.7 cm; natural vertical spread is 4.8 cm; sepal width is 1.6 cm; sepal length is 1.6 cm; petal width is 1.5 cm; petal length is 2.3 cm; labellum width is 2.0 cm; labellum length is 2.3 cm.

*Coloration.*—The dominant flower color appears on the sepals and petals and is PANTONE 1817C (Red). The top and sides of the column is a slightly lighter red, PANTONE 195C. Mid column distally, the underside of the column is white. The labellum is a brighter red, PANTONE 202C, with the top of the crest having a slightly orange tinge, PANTONE 171C. The anther cap is white, PANTONE 7527C, with a red spot 1.5 mm up from the bottom. The dot is red in color, PANTONE 195C, and 1 mm wide×2 mm long. As the flower ages, the anther cap develops inconsistent bright purple spots, PANTONE 241C. The pollinia are completely concealed by the anther cap, and if it is removed the pollinia may be extracted. The pollinia are yellow, PANTONE 129C, but can range in shades of yellow as the plant ages.

Quantity of flowers and time to flower:

*Flower longevity.*—The flowers can last up to 7 weeks on the plant with good environmental conditions. A first bloom plant will produce 25 to 35 flowers depending on environmental conditions.

*Natural flowering season.*—The natural flowering season is early fall.

Fragrance: No fragrance has been detected by the Inventor.

Reproductive organs: The stamens, style and stigmas are fused into a single short structure called the column, possessing one terminal anther with pollen grains united to a pollinia, which are covered by an anther cap. The stigma is located under the column behind the pollinia. The ovary is inferior, with three carpels being present.

*Column.*—The column is erect with wings on either side of the stigma, 2 mm wide by 5 mm long.

*Pollinia.*—Two oval masses of pollen are present, about 1 mm in diameter.

*Stigma.*—The stigma is concave, round, with a high gloss, and sticky.

*Ovary.*—The ovary is about 2.2 cm long by 2.5 mm in diameter.

*Seed.*—Seed production has not been observed.

Disease resistance: Resistance or susceptibility to known pathogens of ×*Wilsonara* has not been observed on plants grown under commercial production conditions.

General observations: Plants of ×*Wilsonara* Red Pacific 'Deep Shadows' produce a pleasing arrangement of many deep red flowers on a panicle that is desirable in size for the size of the plant. The flowers are long lasting and nicely shaped. The plant grows quickly to sexual maturity.

What is claimed is:

1. A new and distinct variety of orchid plant named ×*Wilsonara* Red Pacific 'Deep Shadows', substantially as illustrated and described herein.

* * * * *